United States Patent [19]

Biesel et al.

[11] Patent Number: 5,281,342
[45] Date of Patent: Jan. 25, 1994

[54] METHOD AND APPARATUS FOR THE SEPARATION OF BLOOD INTO ITS COMPONENTS

[75] Inventors: Wolfgang Biesel, Ottweiler; Johannes Geibel, Wadern; Henning Brass, Homburg, all of Fed. Rep. of Germany

[73] Assignee: Fresenius AG, Bad Homberg, Fed. Rep. of Germany

[21] Appl. No.: 932,130

[22] Filed: Aug. 19, 1992

[30] Foreign Application Priority Data

Sep. 6, 1991 [DE] Fed. Rep. of Germany ....... 4129516

[51] Int. Cl.$^5$ ............................................ B01D 21/26
[52] U.S. Cl. ...................................... 210/782; 210/97; 210/138; 210/789; 210/929; 494/1; 494/37
[58] Field of Search ................. 210/87, 97, 143, 195.2, 210/321.65, 88, 321.67, 321.68, 360.1, 512.1, 782, 789, 929, 787, 134, 98, 138; 422/72; 604/4, 5, 6; 494/3, 10, 11, 1, 37, 84

[56] References Cited

U.S. PATENT DOCUMENTS 4,464,167  8/1984  Schoendorfer et al. ............. 494/10
4,806,252  2/1989  Brown et al. ......................... 494/10
5,104,526  4/1992  Brown et al. .......................... 210/94

Primary Examiner—Robert A. Dawson
Assistant Examiner—Sun Uk Kim
Attorney, Agent, or Firm—Robbins, Berliner & Carson

[57] ABSTRACT

The invention concerns a process and a device for more efficiently obtaining a highly pure fraction of thrombocytes during density centrifugation of blood, which no longer has to be filtered before infusion into a patient for leukocytes contained therein, in order to prevent immunization of the recipient. The invention is based on a two-stage density separation, wherein in a first stage a separation is made between cells and thrombocyte-rich plasma, and the thrombocyte-rich plasma is not separated into a thrombocyte concentrate and thrombocyte-poor plasm until a second stage. During the first separation, the position of the phase boundary is changed cyclically in the first separation stage. Through alternating the phase boundary in the first stage, it becomes possible for the first time in the second stage to obtain highly pure thrombocyte concentrations with minimally low leukocyte contamination from the transferred thrombocyte-rich plasma without loss of efficiency.

9 Claims, 3 Drawing Sheets

METHOD AND APPARATUS FOR THE SEPARATION OF BLOOD INTO ITS COMPONENTS

BACKGROUND OF THE INVENTION

The present invention is directed to a process for separation of blood into its components through density centrifugation, wherein in a first separation stage with a monitored phase boundary, the blood is coarsely separated into at least two phases, of which a first fraction consists primarily of blood cells and the second fraction primarily of thrombocyte-rich blood plasma, and wherein in a second separation stage, one of the fractions is further separated for the purpose of obtaining a concentrate of one blood component. The invention further concerns a device for separation of blood into its components through density centrifugation with a first separation stage, the separation chamber, to which the blood to be separated may be delivered on the input side via a blood pump, wherein the blood is coarsely separated into at least two phases, of which the first fraction consists primarily of blood cells and the second fraction primarily of thrombocyte-rich blood plasma, and which has means for detection of the phase boundary between the two fractions with a second separation stage, the collection chamber, to which the thrombocyte-rich blood plasma may be delivered via a plasma pump, and in which this fraction may be further separated for the purpose of obtaining a concentrate of one blood component, and with a program controller for operation of the device including the adjustment of the pump speed of the plasma pump. Preferably, the thrombocyte-rich blood plasma fraction is further separated in the second separation stage for the purpose of obtaining a thrombocyte concentrate.

Such devices have become known, for example, through the cell separator of the applicant Fresenius AS 104, of the Baxter company CS 3000, or the Cobe company Spectra. Specific blood components which are delivered to the patient are needed for the treatment of patients with certain diseases. Thus, for example, thrombocyte concentrates are needed for the treatment of thrombocytopenic patients. For this purpose, the blood of a donor, connected to an extracorporeal circuit, is subjected to density centrifugation in a blood centrifuge, and separated into its components. During this blood separation, in a first stage the blood is coarsely separated into two phases, i.e., into a dark red cell concentrate fraction, which at first consists primarily of erythrocytes, and into a clear, yellowish fraction which consists primarily of thrombocyte-rich blood plasma. The position of the boundary between the two phases is monitored by a detector device and regulated, for example, by a plasma pump. The term "high phase boundary" is used when the volume of cells outbalances the volume of cell-rich plasma, and the term "low phase boundary" is used in the opposite case. In known processes for obtaining thrombocyte concentrates, in the usual mode of operation, after reaching the desired position, the position of the phase boundary is kept constant during the entire duration of the separation.

If one wishes to obtain a thrombocyte concentrate, the thrombocyte-rich plasma is separated in a second stage into thrombocyte-poor plasma and the desired thrombocyte concentrate. The thrombocyte concentrate is used for the treatment of the patient; the remaining components of the blood are recombined and retransfused to the donor.

A standard thrombocyte concentrate, consisting of approximately 3 to $4 \times 10^{11}$ cells, should be obtained with the shortest possible separation period, with the highest possible yield, and the lowest possible contamination by leukocytes. In a foreign organism (in this case, the patient), leukocytes trigger defense mechanisms which can sharply restrict the effectiveness of preparations administered subsequently.

Lymphocytes, a subfraction of the leukocytes (which are the determining factor in triggering the defense mechanisms), and thrombocytes cannot be separated from each other with certainty by centrifugation according to the known processes because of the small difference in size. Consequently, according to the prior art, to assure avoidance of immunization a thrombocyte concentrate is additionally filtered to separate out the leukocytes, before it is transfused to a patient. Comparable measures are performed with other blood components.

Consequently, with the known process an additional processing step in another separation device is necessary, whereby time and cost are disadvantageously increased, also with regard to maintaining sterility.

The object of the invention is to design a process and apparatus such that a blood component, in particular a thrombocyte concentrate, which has extremely low contamination and consequently does not have to be further filtered, can be obtained directly.

SUMMARY OF THE INVENTION

In accordance with the present invention, in a first separation stage during the separation process the phase boundary between the two fractions is shifted alternatingly between at least two positions. In addition, apparatus is provided wherein a program controller 6 comprises a control section for the plasma pump 5, which is designed such that in the separation chamber 1 during the separation process the phase boundary between the two fractions can be shifted alternatingly between at least two positions. Through the alternation of the phase boundaries in the first separation stage, it is possible, in the case of obtaining a thrombocyte concentrate, to deliberately transfer only thrombocytes with thrombocyte-rich plasma into the second separation stage and thus to almost completely eliminate contamination by leukocytes.

It is known, in blood cell separators of the type heretofore employed, to provide a mode of operation with constant separation boundaries, whereby the plasma pump is operated for a short time at an elevated speed compared to the blood pump, and then to return to the original mode of operation. With this "spill-over" mode of operation, a spill-over of the thrombocyte-rich plasma fraction (PRP-fraction) occurs up to passage of the red blood cells. During this time, the plasma pump is operated at an increased speed and stops, for example, upon detection of increased cell density or after transfer of a predefined volume of the fraction to be collected. Consequently, with this spill-over process the phase boundary breaks down, and must then be reset at the preset constant value. In contrast, with the process of the "alternating separation boundary" according to the invention, the separation boundary is alternated between two constant positions at cyclical intervals. The plasma flow rate is changed only during the changing of the separation boundary. The PRP-fraction is transferred into the second stage and blood cells are forced from the separation chamber of the blood cell separator via a second outlet and retransfused to the donor. The process can also be used for obtaining other types of cells of a mixture of cells through separation of other biological fluids.

BRIEF DESCRIPTION OF THE DRAWINGS

The invention may be better understood with reference to the accompanying drawings, in which.

DETAILED DESCRIPTION OF THE INVENTION

Figure 1:
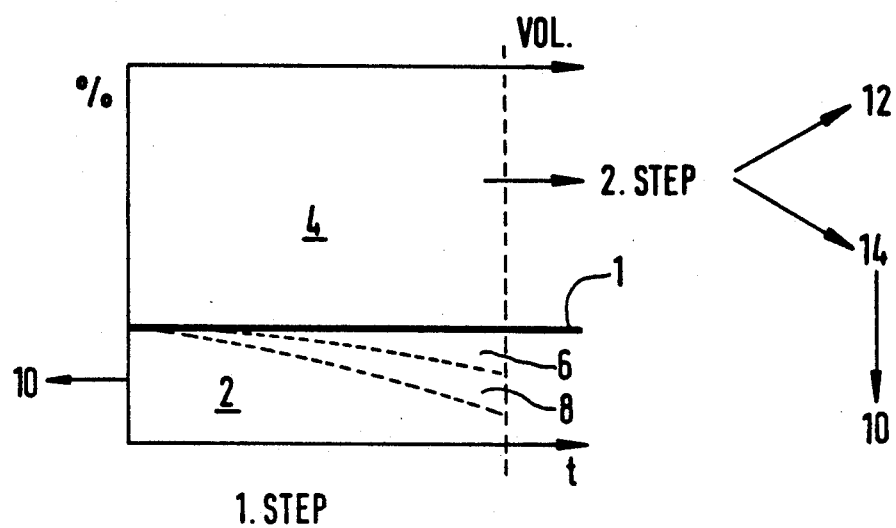
FIG. 1 illustrates schematically the distribution of the phases in a blood centrifuge with a low phase boundary.

Processes and devices for separation of blood into its components through density centrifugation are notoriously well known. They are, for example, known from U.S. Pat. Nos. 3,655,123, 4,056,224 and 4,108,353, to which reference is made. Devices for monitoring the phase boundary in such separation devices (blood centrifuges) are known, for example, from EP Patent 116 716, to whose disclosure reference is made. Consequently, schematic representations in the drawings are adequate for the understanding of the invention.

In FIG. 1, the distribution of the phases in a blood centrifuge at a low separation boundary is schematically represented as a function of the separation time t. During the course of the separation, a layering of the separated blood components forms. Supported on top of erythrocytes 2 and lying beneath a layer of thrombocyte-rich plasma 4, a relatively wide thrombocyte layer 6 forms above a leukocyte layer 8. The schematic representation depicts a hypothetical ideal state of the phase boundary between thrombocytes and leukocytes. In practice, it has been shown that the relatively wide thrombocyte layer is capable of forming a barrier against the leukocyte layer. The erythrocytes are returned to the donor 10, and only the thrombocyte-rich plasma 4 is transferred to a second separation stage. In this stage the thrombocytes are concentrated (position 12) and, after thorough mixing with the erythrocytes 2 from the first stage, the thrombocyte-poor plasma 14 is returned to the donor 10.

Figure 2:
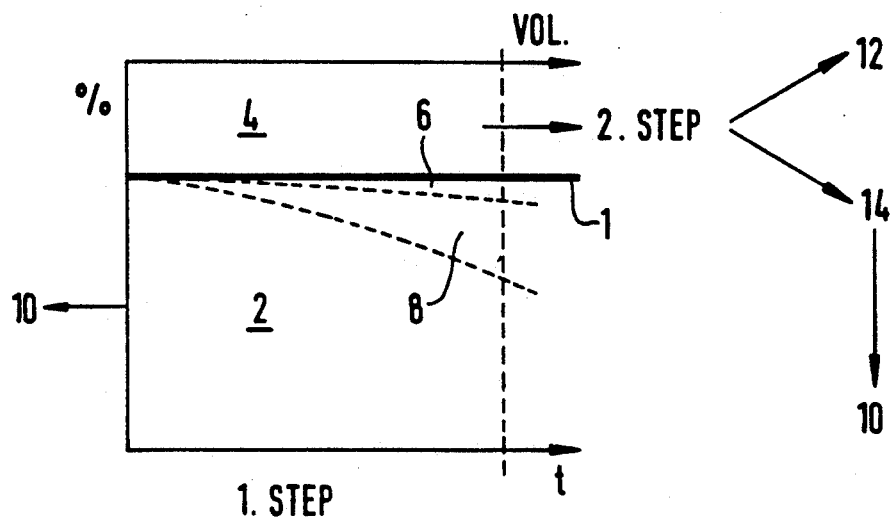
FIG. 2 is a schematic representation according to FIG. 1, but with a high phase boundary.

FIG. 2 schematically depicts the distribution of the separated components with a high phase boundary. The reference numbers are selected as in FIG. 1. The phase boundary 1, also called a separation boundary, can be shifted and regulated with known means, for example, by different discharge of the plasma fraction by means of a plasma pump.

In contrast to the separation with a low phase boundary (FIG. 1), the layer of thrombocytes 6 forms a smaller barrier against the layer of white blood cells 8 (leukocytes). Due to the higher flow speed in the plasma layer, sedimentation of the blood cells is rendered difficult. For this reason, among others, it is significantly easier for contamination of the thrombocyte-rich plasma 4 with white blood cells 8 to occur.

Over the course of a separation, the composition of the cell concentrate within the first separation stage changes. Table 1 shows the portion of the blood fractions by percentage based on the amount of blood processed at the middle position of the separation boundary, with the abbreviations used for the blood fractions having the following meaning: PRP=thrombocyte-rich plasma; PLT=thrombocytes; WBC=leukocytes; RBC=erythrocytes.

TABLE 1

| Blood volume | PRP | PLT | WBC | RBC |
| --- | --- | --- | --- | --- |
| 200 ml | 40 | 2 | 5 | 53 |
| 1,000 ml | 40 | 10 | 15 | 35 |
| 3,000 ml | 40 | 20 | 30 | 10 |

With a constant separation boundary position, according to Table 1, an agglomeration of an intermediate phase, consisting primarily of thrombocytes and leukocytes, occurs in the separation chamber. Plasma is discharged to regulate the phase boundary and erythrocytes are forced out of the separation chamber of the blood centrifuge.

Experience has shown that a loss in yield of thrombocytes in the second stage is linked with a constantly low separation boundary position in the first separation stage. On the other hand, a transfer of leukocytes is prevented here and low leukocyte contamination in the thrombocyte concentrate is thus assured.

It is true that the number of thrombocytes increases in the second stage with a constantly high separation boundary position in the first separation stage, but so does the number of leukocytes and with that the contamination in the thrombocyte concentrate. At an extremely high phase boundary, the contamination increases sharply, as the following table, presenting the efficiency and leukocyte contamination (WBC) of thrombocytophoreses with constant and alternating separation boundary positions, shows.

TABLE 2

| | Constant phase boundary | | Altern. phase boundary |
| --- | --- | --- | --- |
| Averages | high | extremely high | low/extremely high |
| Efficiency % | 40.8 | 43.9 | 39.1 |
| WBC contamination *10 E6 | 3.8 | 128.6 | 0.34 |

Because of increased flow speed in the plasma layer, sedimentation of thrombocytes is not possible, and eddies and increased mixing with the leukocyte layer occur, such that leukocytes can be transferred into the second stage with thrombocytes. The separation efficiency relative to thrombocytes reaches maximally high values; however, in the extreme case the contamination is increased about one-hundredfold. Separation efficiency is defined here as the relationship between yield and supply of the desired type of cells, expressed as a percent. The supply of a type of cell is defined by determining the average concentration of the cell type in the blood volume presented, the yield by determining the concentration of the cell type in the volume of the concentrate obtained.

By alternation of the separation boundary position between at least two positions during the separation process in the first separation stage, the process according to the invention provides for creation of a collection time and a transfer time. During the collection time, a low to high separation boundary is preferably set, such that an agglomeration of thrombocytes occurs in the intermediate phase. Most of the thrombocytes are continuously transferred into the second stage with the thrombocyte-rich plasma. The separated cells are forced out of the separation stage.

In the transfer time, the phase boundary is extremely high such that the thrombocytes collected in the first stage are spilled over along with it. A certain residual portion of the blood platelet layer remains in the chamber and prevents passage of the leukocytes.

It is true that the efficiency of the separation using the process is somewhat reduced by a certain quantity of thrombocytes; however, the leukocyte contamination can be held far below the critical immunological limit and thus an additional purification stage can be avoided.

Figure 3:
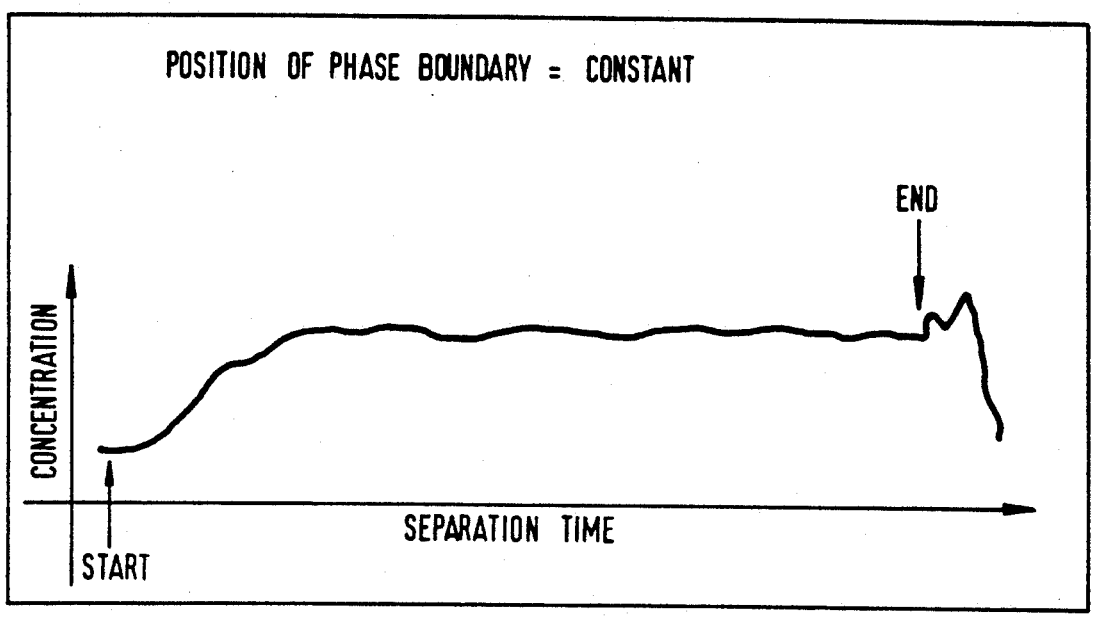
FIG. 3 is a diagram in which the thrombocyte concentration is plotted on the ordinate against the separation time on the abscissa, with a constant position of the phase boundary.
Figure 4:
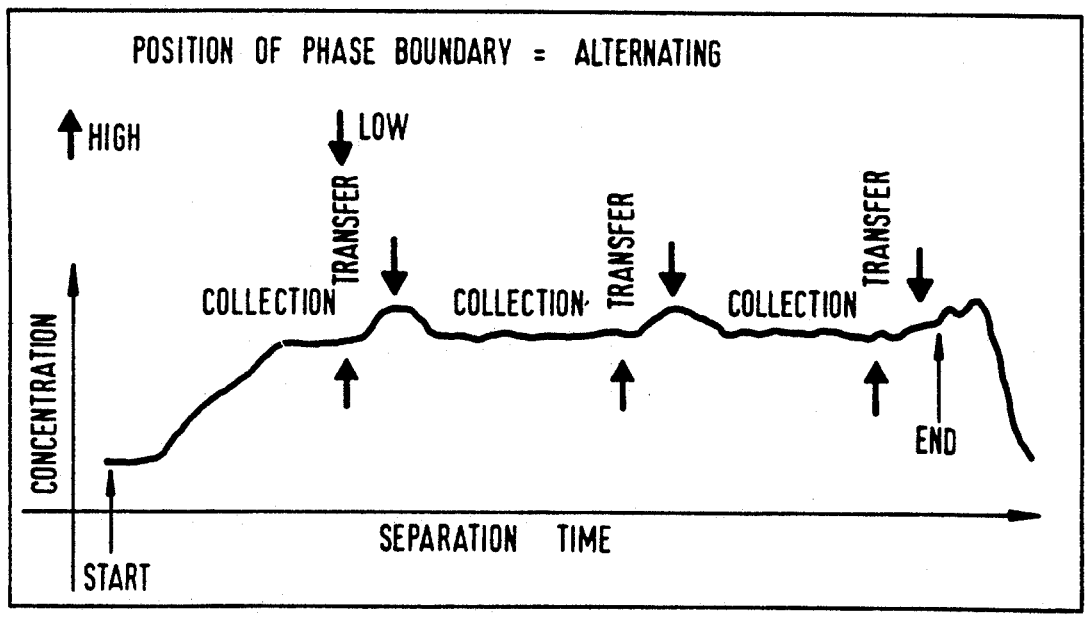
FIG. 4 is a diagram corresponding to FIG. 3, but with an alternating phase boundary.

FIG. 4 depicts a diagram with the thrombocyte concentration plotted on the ordinate against the separation time on the abscissa, with alternating phase boundaries according to the invention. FIG. 3 depicts a corresponding diagram, but with a constant position of the phase boundary in the first separation stage according to the prior art. A comparison of the two diagrams clearly reveals an increase in thrombocytes in the transfer phase zone (FIG. 4).

Due to the initially low separation boundary as well as the change of the position of the separation boundary and the resultant altered flow relationships in the chamber, leukocytes are eliminated from the chamber via the cell outlet. Thus, during the time of the high separation boundary, there is no risk of contamination of the thrombocyte-rich plasma and consequently of the thrombocyte concentrate then obtained from it. However, in this phase the proportion of thrombocytes transferred into the second stage is significantly increased, as shown in FIG. 4.

The time of the high separation boundary, called the transfer phase in FIG. 4, is relatively short compared to the time of the low separation phase, called the collection phase in FIG. 4, since during this time a new agglomeration of leukocytes, among other things, begins.

The determination of reasonable phase lengths and separation boundary positions can be accomplished empirically and is then preset in the respective separation program of the separation device.

Figure 5:
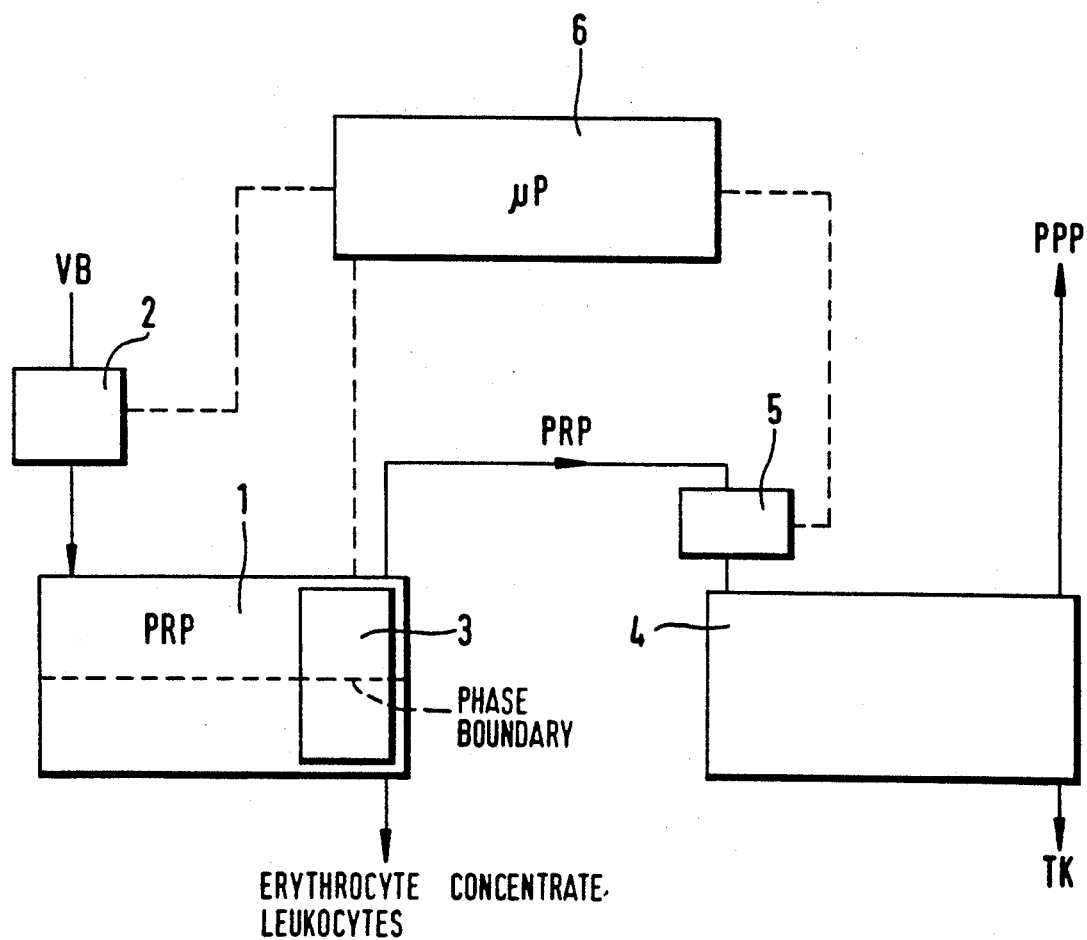
FIG. 5 is a block diagram of a blood cell separator (blood centrifuge).

FIG. 5 schematically depicts a blood centrifuge by means of which the process according to the invention may be performed. For the sake of clarity, only the essential components of this blood centrifuge are shown. The blood centrifuge, also called a blood separator, has a first separation stage, a separation chamber 1, into which the blood to be separated, the so-called "whole blood" VB, can be introduced on the input side via a blood pump 2. In this separation chamber 1, the whole blood is coarsely separated into two phases. The first fraction consists preferably of blood cells, in particular of the erythrocytes RBC. The second fraction consists preferably of the thrombocyte-rich blood plasma PRP. Additional details on the individual fractions and their changes as a function of separation time can be found in FIG. 1 and 2 in conjunction with Tables 1 and 2. The separation chamber 1 has a device 3 for detection of the phase boundary between the two fractions, the so-called "phase detector".

The blood centrifuge also has a second separation stage, a collection chamber 4, into which the thrombocyte-rich blood plasma fraction PRP can be introduced via a plasma pump 5. In this collection chamber the PRP fraction is further separated for the purpose of obtaining the thrombocyte concentrate TK. A platelet/thrombocyte-poor plasma fraction (PPP) is also recovered.

The blood centrifuge also has a program controller 6, which usually consists of a microprocessor (denominated "$\mu P$" in FIG. 5). This controller is linked to all essential sensors and positioning elements of the blood centrifuge and controls all operational states. The connection between the phase detector 3 and the program controller 6 and from the latter to the plasma pump 5 is as a rule designed such that the flow rate of the plasma pump is changed as soon as a shift in the position of the phase boundary occurs or is supposed to occur.

The adjustment of the phase boundary between the two fractions in the separation chamber is performed by presetting the relationship between the flow rates of the plasma pump and the blood pump. If the blood centrifuge is in the steady state at the lower separation phase, the blood pump and the plasma pump deliver in a first preset relationship (e.g., 50/20). If the phase boundary is supposed to be raised, this relationship must be changed in favor of the plasma delivery rate. The program controller makes the necessary adjustments. Usually, the plasma pump is also raised. As soon as the upper predefined separation boundary is reached, the pump delivers in the original relationship (e.g., 50/20).

With the reduction there is an inversely proportional control. The plasma pump is adjusted to a lower pump speed, thus pumps out less, until the lower separation boundary is obtained.

According to the invention the program controller has a control section for the plasma pump 5 which is designed such that in the separation chamber 1 during the separation process the phase boundary between the two fractions can be shifted alternatingly between at least two positions. This control section has a first time interval for the adjustment of a lower to higher phase boundary and a second interval for the setting of an extremely high phase boundary. The first of these time intervals, the collection interval, is longer than the second time interval, the transfer interval.

Process control of the blood centrifuge oriented to the accumulated thrombocyte quantity of the respective individual donor is even possible; thus, individual differences in the donor blood, such as blood platelet size, platelet concentration, etc. can be taken into account.

What is claimed is:

1. A process for separation of blood into blood components by density centrifugation, comprising:
   separating the blood coarsely in a first separation stage into at least two phases, of which a first fraction consists primarily of blood cells and a second fraction consists primarily of thrombocyte-rich blood plasma, a phase boundary between the fractions being shifted alternatingly between at least two positions during separation of the blood in said first separation stage; and
   separating at least one of said first and second fractions further in a second separation stage to obtain a concentrate of a blood component.

2. The process according to claim 1, wherein for a first time interval a low to high phase boundary is set, and for a second time interval an extremely high phase boundary is set.

3. The process according to claim 2, wherein the first interval is a collection interval and is longer than the second, transfer interval.

4. The process according to claim 3, wherein the determination of the time intervals and/or the phase boundary positions is performed empirically.

5. The process according to claim 3, wherein the determination of the time intervals and/or the phase boundary positions is performed as a function of the accumulated quantity of the blood component to be obtained.

6. The process according to claim 3, wherein for the duration of the separation at least 2 collection intervals and at least 2 transfer intervals are provided in succession.

7. A device for separation of blood into blood components by density centrifugation, comprising:
 a first separation stage including a separation chamber and blood pump means for introducing blood into the separation chamber, in which the blood is coarsely separated into at least two phases, of which a first fraction consists primarily of blood cells and a second fraction consists primarily of thrombocyte-rich blood plasma; and
 a second separation stage including a collection chamber and plasma pump means for delivering thrombocyte-rich blood plasma in the second fraction into the collection chamber for separating the second fraction further to obtain a concentrate of a blood component; and
 program controller means for operation of the device including adjustment of the pump speed of the plasma pump means, wherein the program controller means includes a control means for controlling the plasma pump means to shift a phase boundary between the two fractions in the separation chamber alternatingly between at least two positions during separation of the blood in the first separation stage.

8. The device according to claim 7, wherein the control means includes means for setting a low to high phase boundary during a first time interval and an extremely high phase boundary during a second interval.

9. The device according to claim 8, wherein the boundary setting means sets the first interval longer than the second interval.

* * * * *